United States Patent [19]

Bommarius et al.

[11] Patent Number: 5,554,518
[45] Date of Patent: Sep. 10, 1996

[54] STABILIZED METAL-ION-ACTIVATED L-ARGINASE (L-ARGININE AMIDINO HYDROLASE E.C.3.5.3.1)

[75] Inventors: Andreas Bommarius, Frankfurt am Main; Karlheinz Drauz; Kyriakos Makryaleas, both of Freigericht, all of Germany

[73] Assignee: Degussa Aktiengesellchaft, Frankfurt am Main, Germany

[21] Appl. No.: 323,609

[22] Filed: Oct. 17, 1994

Related U.S. Application Data

[63] Continuation of Ser. No. 894,769, Jun. 10, 1992, abandoned.

[30] Foreign Application Priority Data

Jun. 10, 1991 [DE] Germany ............... 41 19 029.7

[51] Int. Cl.$^6$ ............... C12P 13/10; C12N 9/80
[52] U.S. Cl. ............ 435/114; 435/128; 435/188; 435/227
[58] Field of Search ............... 435/128, 188, 435/227, 114

[56] References Cited

U.S. PATENT DOCUMENTS 4,354,913  10/1982  Pungor et al. ............ 435/177
4,898,886   2/1990  Amat-Larraz ............ 514/588

FOREIGN PATENT DOCUMENTS 0464325  12/1991  European Pat. Off. .

OTHER PUBLICATIONS

European Search Report.
Article entitled "Biomedica Biochemica Acta" vol. 50—1991 No. 10/11 Akademie Verlag First Int'l Workshop on Enzymes in Peptide Synthesis pp.249–255.
Japanese Chemical Abstract JP48026976.
Article from Biotechnology Techniques vol. 4 No. 2 133–136 (1990) Received Jan. 12th entitled "A Simple and Rapid High Recovery Protocol for the Purification of Arginase" by N. B. Patil et al.
Article entitled "Purification, Properties and Subunit Structure of Arginase from Iris Bulbs"by Jean–Pierre Boutin Eur. J. Biochem. 127, 237–243 Feb. 1982.
Article entitled "Subunit Interactions and Immobilised Dimers of Human Liver Arginase" by Nelso Carvajal et al. Biochimica et Biophysica Acta 527 (1978) 1–7.
Article entitled "The Role of Metal Ions in the Activation of Arginase" by Megumu Munakata et al. Bioinorganic Chemistry 6, 133–142 (1976).
Falba et al., Ascorbinsaure, Rompp Chemie Lexikon, 9th Ed., Nov. 1989, pp. 265–266.
Neumuller, Otto–ALbrecht; Butylhydroxyanisol; Rompps Chemie–Lexicon, 7th Ed., 1976, p. 456.
CA vol. 93, 1980, 245446Y.
Yamane et al., Evaluation of Half–Life of Immobilized Enzyme During Continuous Reaction in Bioreactors: A Theoretical Study, Biotechnology and Bioengineering, vol. 30, pp. 963–969 (1987).
Promega Catalogue, 1991–1992, p. 342.
Stryer, *Biochemistry*, New York: Freeman & Co., 1988, p. 268.
Bommarius et al, Biomed Biochim. Acta, 50 (10/11):S249–S255, (1991).
Greenberg, "Arginaes", *The Enzymes,* 2nd ed., 1960, Academic Press, New York, Ch. 14, 257–67.
Roholt et al, Archives of Biochem. and Biophys., 62:454–470, (1956).

*Primary Examiner*—Herbert J. Lilling
*Attorney, Agent, or Firm*—Cushman Darby & Cushman

[57] ABSTRACT

An arginase batch capable of producing ornithine with reduced consumption of enzyme. The arginase batch is stabilized by the addition of a reducing agent in at least a 10-fold molar amount relative to the arginase.

9 Claims, 2 Drawing Sheets

FIG. I

STABILIZED METAL-ION-ACTIVATED L-ARGINASE (L-ARGININE AMIDINO HYDROLASE E.C.3.5.3.1)

This is a continuation of application Ser. No. 07/894,769, filed on Jun. 10, 1992, which was abandoned upon the filing hereof.

The present invention relates to a stabilized arginase batch, a method for the enzymatic conversion of arginine to ornithine in aqueous solution and an arginase kit useful for this purpose.

BACKGROUND OF THE INVENTION

Arginase (L-arginase, L-arginine amidino hydrolase: E. C. 3.5.3.1) is an enzyme which has been known for more than 50 years and which catalyzes the enzymatic production of L-ornithine from L-arginine. This catalysis takes place in vivo in the liver of mammals in the last stage of the urea cycle, during which urea and L-ornithine (2,5-diaminopentanoic acid) are formed by hydrolysis from (L-arginine 2-amino-5-guanidino pentanoic acid). The enzyme can correspondingly be obtained from mammal liver, e.g. calf's liver; however, it also occurs in the flora kingdom as well as in several microorganisms.

Arginase has a molecular weight of approximately 138,000 and consists of 4 identical subunits. $Mn^{2+}$ as well as $Co^{2+}$ and $Ni^{2+}$ can be added as typical activator.

L-ornithine is an amino acid which occurs in the body of mammals but is not produced during anabolism and is therefore not incorporated in proteins, that is, a natural but non-proteinogenic amino acid.

L-ornithine can replace L-arginine, an amino acid essential in infants and children, in all functions. Since the salts of L-ornithine entail a lesser stressing with urea of the organism and exhibit in part a better solubility behavior than L-arginine, L-ornithine has considerable commercial potential. A deficiency of arginine or ornithine can result in injury, in some cases in death, e.g. by means of an elevated ammonia level on account of high amino acid adsorption after a period of fasting or malnutrition.

Arginase has long been used as a diagnostic enzyme. However, this enzyme could not be used hitherto for the production of L-ornithine from L-arginine on an industrial scale since it exhibits only a very slight stability under reaction conditions and correspondingly can not be recovered or can be recovered only to a slight extent from an enzyme batch. Therefore, because of the high enzyme expense, the enzymatic production of L-ornithine from L-arginine is not cost effective on an industrial scale.

Therefore, the only potential candidates for industrial production of L-ornithine and its salts have included only fermentation from glucose with strains of Brevibacterium, Corynebacterium and Arthobacter, and the chemical hydrolysis of L-arginine in addition to the enzymatic method. However, the chemical hydrolysis results in many byproducts, e.g. in the partial hydrolysis to L-citrulline (2-amino-5-ureido pentanoic acid) or in the racemization of L-arginine or L-ornithine. Fermentation to L-ornithine is economical only in high tonnages.

Although arginase exhibits a satisfactory activity and selectivity for the hydrolysis of L-arginine to L-ornithine, the stability of the enzyme for industrial use is insufficient. In order to obtain good activity, the addition of bivalent manganese ions in addition to the enzyme to the reaction solution is necessary. However, when the reaction is carried out at the generally adjusted pH of the reaction of 9.5, which corresponds to the activity optimum of arginase published in the literature, the oxidation of bivalent manganese to tetravalent manganese frequently causes precipitatation of manganese dioxide after a brief time. A deactivation of the arginase also occurs (M. Munakata et al., Bioinorganic Chemistry 1976, 6, pp. 133–42; V. Rossi et al., Int. J. Peptide Protein Res. 1983, 22, pp. 239–50).

SUMMARY OF THE INVENTION

The object of the present invention is to provide a stabilized form of an arginase batch which can be used in a rather broad pH range without becoming excessively deactivated. A further object of the invention is to provide arginase in a form which can be separated after the reaction for reuse. A still further object of the invention is to provide a corresponding arginase kit and a method for the enzymatic conversion of L-arginine to L-ornithine in solution in which method the arginase can be reused.

These and other objects are provided by a stabilized arginase batch which contains a reducing agent dissolved in the water in a molar concentration which is at least 10-fold relative to the arginase.

As used herein, the term "arginase batch" refers to a composition which contains, dissolved in water, the enzyme arginase, a substrate which is to be converted by the enzyme and, if necessary, $Mn^{2+}$. In accordance with the present invention, the arginase batch also contains a reducing agent in a molar concentration at least tenfold times the concentration of the arginase.

For reasons of concentration and expense, a molar amount of the reducing agent $10^6$ times greater than the enzyme is set as upper limit of the excess. Additions of the reducing agent in $10^2$ to $10^4$-fold excess relative to the arginase are advantageous; the reducing agent is advantageously present in a concentration of $10^{-7}$–$10^{-1}$ moles/liter, preferably $10^{-5}$–$10^{-3}$. Mercaptoethanol, dithiothreitol and, especially advantageously, ascorbic acid (L-ascorbic acid, vitamin C) have proven to be effective reducing agents.

The arginase reaction takes place preferably at a $10^{-8}$ to $10^{-5}$ molar concentration (moles/liter) of arginase. It is advantageous for good arginase activity if $Mn^{2+}$ ions are present in a 10 to $10^6$-fold excess relative to the arginase. The solvent is preferably purely aqueous. The enzyme, e.g. arginase from calf's liver, is advantageously used between 1000 and 10,000 U/l; $Mn^{2+}$ is added preferably between $10^{-4}$ and $10^{-2}$ moles/liter, preferably as manganese sulfate. It has been determined, in this connection, that an especially good stability of the arginase is achieved at a stoichiometric deficiency of the reducing agent relative to the $Mn^{2+}$ ions, especially at a molar ratio between reducing agent to $Mn^{2+}$ ions of 0.01–0.9. The stability is greatest if the molar ratio of reducing agent to $Mn^{2+}$ ions is between 0.1 and 0.5. These ratios are especially preferred if the arginase reaction is started at a pH of 8.5–10.5. The pH can be adjusted to 8.5–10.5 by the addition of acids (e.g. $H_2SO_4$ or HCl) to the arginine solution; acid, arginine and/or ornithine form a buffer system.

It is advantageous to add 0.1 to 2.0 moles/l arginine to the arginase batch as substrate, in which instance a saturated solution containing undissolved arginine can be present. In the case of buffer-free batches, the ornithine formed can also precipitate. In particular, arginine concentrations between 0.5 to 1.5 moles/l, optimally up to 1.0 mole/l, have have been established as providing good arginase activity and high recovery rates of arginase. The arginine solution does not have to be buffered, that is, the initial pH of the solution may be approximately above 10.5 up to 11.5, preferably 11 to 11.5. This value is determined primarily by the intrinsic pH of the arginine. This pH then drops in the course of the reaction to approximately 9.5, conditioned by the conversion of arginine to ornithine. Especially at this initial pH, the concentration of the reducing agent should be at least $10^{-5}$ moles/l.

It was found in this connection that, contrary to the pH optimum of 9.5 described in the literature, the enzyme is active for at least two days and even displays its greatest activity at pH's up 11.5.

The method of the invention for the enzymatic conversion of arginine to ornithine is therefore carried out by reacting arginine (optionally only partially dissolved) in aqueous solution with an arginase and optionally in the presence of $Mn^{2+}$ and optionally in the presence of a buffer system and that a reducing agent is present in the solution in at least a 10-fold molar amount relative to the arginase. In principle, the special requirements of the above-described arginase batch apply in a corresponding manner to the preferred measures of the method of the invention.

The reaction should take place in a quiescent solution, i.e., not agitated or shaken, since the shear forces which occur in a moving solution can deactivate the enzyme. The reaction time is customarily 24–72 hours, which provides total conversion of the L-arginine. The progress of the reaction can be followed, in particular in the case of non-buffered batches, using the decrease of the pH—the pH drops toward the end of the reaction to approximately 9.5, the intrinsic pH of the L-ornithine which is being produced.

The addition of the reducing agent in accordance with the invention, therefore, permits using arginase batches having a considerably broader pH range than is the case with arginase batches without reducing agent, in which the pH should be close to 9.5. This has the advantage that one can work with higher initial arginine concentrations and without an additional buffer system and nevertheless high recovery rates of arginine permit converting several batches with a single quantity of enzyme. Working in buffer-free or buffer-poor systems has the advantage of decreasing the salt concentration in the process. In contrast to the previous arginase batches, the addition of the reducing agent lowers the deactivation of arginase to less than one tenth of the values observed without addition of reducing agent, that is, the arginase is stabilized by at least a factor of 10 by the addition of reducing agent in accordance with the invention.

The stabilization can be expressed as enzyme consumption number, that is, as consumption of units of arginase per kg of ornithine produced during the recycling of the enzyme from each batch. This consumption number is, for an arginase batch using conditions as in Example 1, 5890 with pump motion without reducing agent, 5000 without pump motion without reducing agent and 270 without pump motion with reducing agent.

This stabilization renders possible an economic recovery of arginase after the reaction, which can proceed practically completely. Although according to the literature L-ornithine inhibits arginase, the influence is not controlling in the reaction of the invention. For recovery, the enzyme from the arginase batch is separated from the lower-molecular components at least to a large extent by means of ultrafiltration, preferably with a capillary ultrafiltration flowthrough cartridge (e.g. Romicon, separation limit 10,000 daltons). The batch flows in the cartridge with precipitated manganese dioxide through the capillaries, at which time the greatest part of the solution with the lower-molecular, dissolved components penetrates the pores of the capillaries and the enzyme together with the precipitated manganese dioxide in a small part of the batch (of the solution) leaves the capillaries at the discharge end in concentrated form. The manganese dioxide can be subsequently separated from the enzyme, preferably by filtration. The separated enzyme can be immediately reacted again with L-arginine in the same manner or stored for later use.

It is possible that this unusually high stabilization arises, among other things, because of the fact that the reducing agent partially prevents the oxidation of the $Mn^{2+}$ to $Mn^{4+}$, yet the oxidation must not be totally prevented since small amounts of $Mn^{4+}$ are probably favorable for the activity of the enzyme. That is to say, given a relatively low pH, that is, between 8.5 and 10.5, the reducing agent should be present in a deficiency relative to the $Mn^{2+/4+}$ system in order that the oxidation of the $Mn^{2+}$ is not totally prevented. On the other hand, in the case of a higher pH, in the present instance up to approximately 11.5, the reducing agents which can be customarily used in enzyme reactions are not sufficiently strong to totally prevent the oxidation of the $Mn^{2+}$; correspondingly, even an excess of reducing agent relative to the $Mn^{2+}$ can be used in that case. The pH and the reducing agent should therefore be coordinated in such a manner with one another that a slow precipitation of manganese dioxide is assured, since this probably results in a buildup of a protective layer on the ultrafiltration membrane via which the enzyme can be separated again from the educts and products. The ultrafiltration membrane can be arranged and operated in an enzyme membrane reactor or also as separate unit. The reduction is therefore carried out with advantage in the presence of $MnO_2$, which can also be formed during the reaction.

The components necessary or advantageous for the arginase batch are so stable individually and in mixture or in partial mixture that they can be advantageously offered and stored as a kit. That is, a kit contains amounts of arginase and reducing agent which are coordinated with one another. It is advantageous if the kit also contains $Mn^{2+}$ as e.g. manganese sulfate or manganese chloride and/or optionally also a substrate such as arginine as well as optionally also L-ornithine. L-ornithine is a competitive inhibitor of the enzyme but functions as a stabilizer during the storage of arginase (in solution and in lyophilized form). Then, in order to prepare the batch, the kit needs only to be dissolved in the appropriate amount of preferably sterilized water. The kit can also comprise a part of the required devices such as e.g. capillary ultrafiltration cartridges, especially if disposable products are desired.

DETAILED DESCRIPTION OF PREFERRED EMBODIMENTS

The invention is described further below in examples and drawings, in which.

Figure 1:
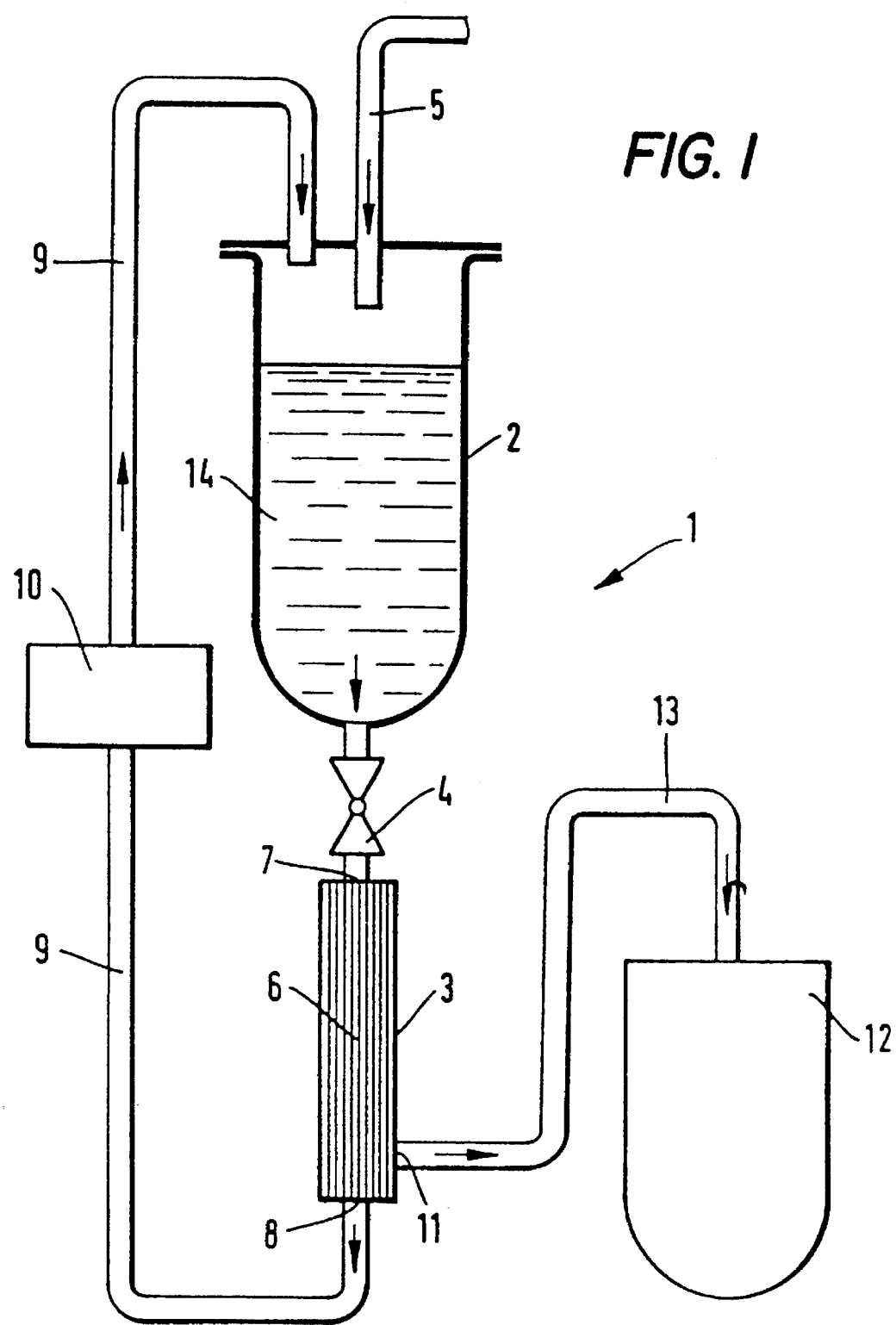
FIG. 1 shows an apparatus for an arginase batch.

The batch ultrafiltration reactor 1 in FIG. 1 comprises reaction vessel 2 and ultrafiltration cartridge 3, which are connected to each other via valve 4. Reaction vessel 2 which contains reaction batch 14, can be sealed and is connected to pressure line 5. After the reaction is over, reaction batch 14 can be forced, without great turbulence, by nitrogen supplied via pressure line 5 and with open valve 4, through cartridge 3. Cartridge 3 comprises a plurality of porous capillaries 6 whose one end 7 is connected via valve 4 to reaction vessel 2 and whose other end 8 is connected to return line 9, via which the enzyme which passed the capillaries can be returned into reaction vessel 2. Filter 10 is located in return line 9 for separating the manganese dioxide which passed cartridge 3. The capillary exterior is connected via discharge 11 to product storage tank 12, in which the lower-molecular components of reaction batch 14 (ornithine, optionally non-converted arginine, buffer salts, reduction agent residues and $Mn^{2+}$) are collected.

An arginase batch can be charged with the returned enzyme.

Figure 2:
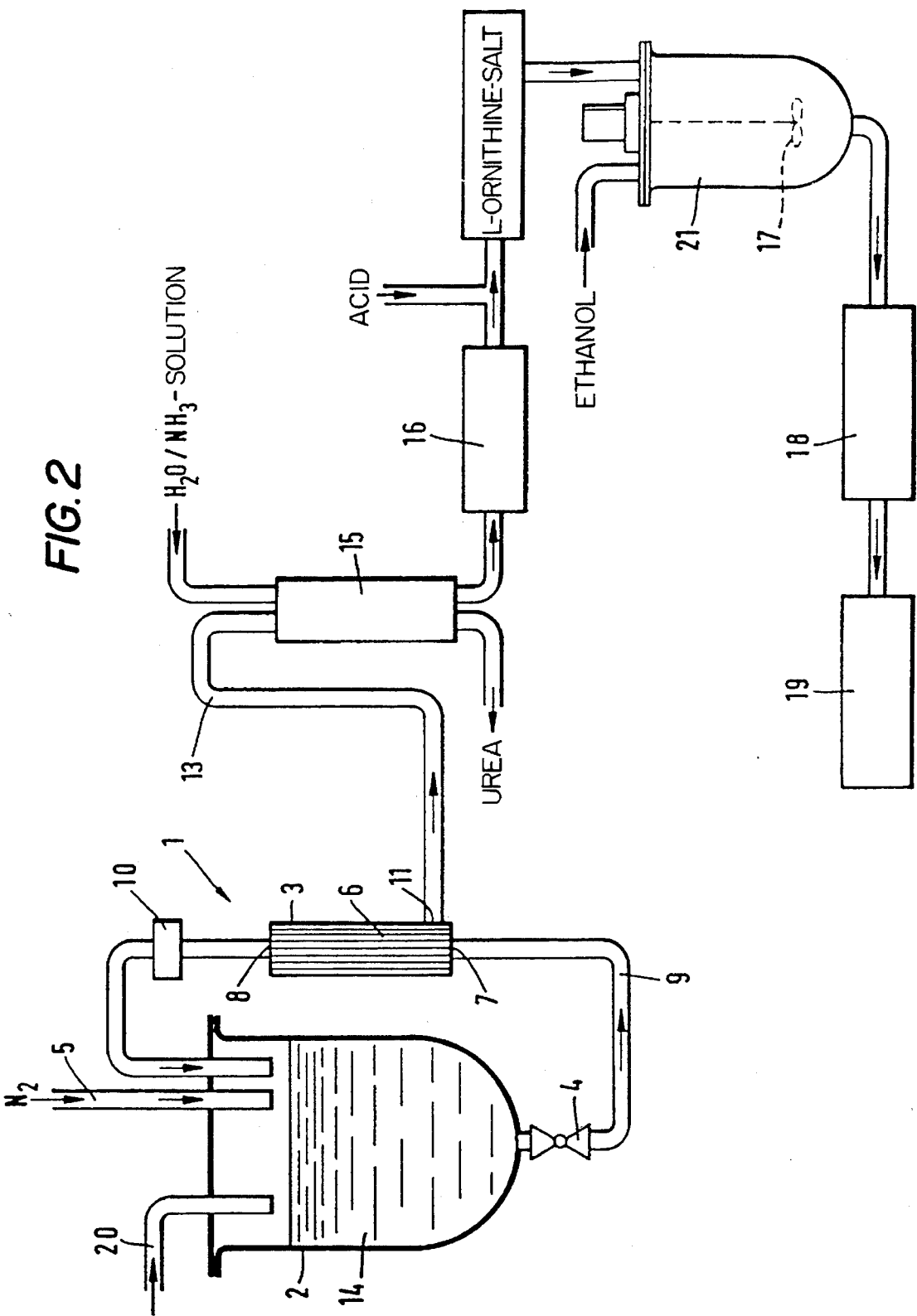
FIG. 2 shows a method for the enzymatic production of ornithine from arginine.

The method illustrated in FIG. 2 comprises batch ultrafiltration reactor 1, which is similar to the reactor shown in FIG. 1. However, discharge 11 of cartridge 3 is connected to cation exchange column 15, on which the ornithine of the filtrate on cartridge 3 is retained whereas urea and anions pass the column. Column 15 charged with ornithine is washed and eluted with ammonia solution. The eluted ornithine is concentrated until saturation of the solution in container 16, neutralized with acid (e.g. HCl, $H_2SO_4$, L-aspartate, α-ketoglutaric acid, acetic acid) until adjusted to be weakly acidic and is combined in precipitation container 21 with approximately threefold the amount of ethanol. The corresponding ornithine salt precipitates thereby, with agitation by stirrer 17, is separated via filter 18 and brought in drier 19 to the desired degree of dryness. Each new batch is supplemented via closable opening 20 in reaction vessel 2 with the appropriate components (consumed enzyme, $H_2O$, reducing agent, etc).

EXAMPLE 1

$2.5 \times 10^{-4}$ moles manganese sulfate×$H_2O$, one half of an equivalent, that is, $1.25 \times 10^{-4}$ moles ascorbic acid, as well as 10,000 units calf's liver arginase (Boehringer Mannheim, Germany) are added to 1 liter of a 0.75 molar solution of L-arginine which had been adjusted with sulfuric acid to pH 9.5. After 24 hours, the conversion of L-arginine was 98% and after a further 24 hours 100%.

After ultrafiltration via a hollow fiber module (Amicon, MWCO 10,000, 0.03 m²), the filtrate was placed over an acidic ion exchanger, eluted with approximately 1 liter 5% ammonia, concentrated by evaporation to 500 ml, adjusted with approximately 26–28 ml concentrated sulfuric acid to a pH of 6.9 and the ornithine sulfate precipitated with 1.5 liter ethanol. 114.3 g pure ornithine sulfate were obtained (84.6% of theory).

EXAMPLE 2

A procedure analogous to that of Example 1 was used, but a concentration of L-arginine of 0.5 mole/l and 6600 units of the enzyme were used. 82.2 g L-ornithine sulfate (91.3% of theory) were obtained.

EXAMPLE 3

A procedure analogous to that of Example 1 was used, but a concentration of L-arginine of 1 mole/l and 9400 units of calf's liver arginase were used. The yield of L-ornithine sulfate was 141.4 g (78.5% of theory).

EXAMPLE 4

30 ml of a 0.75 molar L-arginine solution were combined with $2.5 \times 10^{-4}$ moles manganese sulfate×$H_2O$ with various amounts of ascorbic acid and mixed with 370 units calf's liver arginase once at the intrinsic pH of arginine (approximately pH 11.5) and once stabilized with hydrochloric acid at an initial pH of 9.5. After 23 hours at room temperature, the conversions of arginine were determined. The enzyme was then separated via an ultrafilter and reused in the next batch.

Initial pH 9.5

| Batch No. | Clean Membrane | | Clean Membrane | | |
|---|---|---|---|---|---|
| | Conversion (%) | Asorbic Acid (mol./l) | Conversion (%) | Ascorbic Acid (mol/l) | Loss of Manganese Dioxide |
| 1 | 52 | $2.5 \times 10^{-4}$ | 67 | $1.25 \times 10^{-4}$ | |
| 2 | 37 | | 56 | $1.25 \times 10^{-4}$ | |
| 3 | 13 | | 41 | $1.25 \times 10^{-4}$ | |
| 4 | 7 | | 37 | $1.25 \times 10^{-4}$ | |
| 5 | 4 | | 30 | 0 | * |
| 6 | 0 | | 29 | 0 | * |
| 7 | — | | 29 | 0 | * |
| 8 | — | | 28 | 0 | * |

Initial pH 9.5

Membrane Coated With Manganese Dioxide

| Batch No. | Conversion (%) | Ascorbic Acid (mole/l) |
|---|---|---|
| 1 | 59 | $2.5 \times 10^{-4}$ |
| 2 | 31 | |
| 3 | 19 | |
| 4 | 16 | |
| 5 | 12 | |
| 6 | 10 | |
| 7 | 8 | |
| 8 | 7 | |

Initial pH 11.5

| Batch No. 4 | Membrane Coated With Manganese Dioxide | | Clean Membrane | |
|---|---|---|---|---|
| | Conversion (%) | Acorbic Acid (mol/l) | Conversion (%) | Ascorbic Acid (mol/l) |
| 1 | 79 | $2.5 \times 10^{-4}$ | 79 | $2.5 \times 10^{-4}$ |
| 2 | 73 | | 73 | |
| 3 | 69 | | 72 | |
| 4 | 70 | | 65 | |
| 5 | 67 | | 61 | |
| 6 | 66 | | 61 | |
| 7 | 66 | | 62 | |
| 8 | 66 | | 61 | |

At an initial pH of 9.5, the enzyme is deactivated both in the case of a membrane initially coated with manganese dioxide and in the case of a clean membrane because, at this pH and with sufficient ascorbic acid, the membrane cannot hold a manganese dioxide coating. However, if ascorbic acid is not added, or if insufficient ascorbic acid is added, a layer of manganese dioxide forms and the enzyme is no longer strongly deactivated. At pH 11.5, however, a layer of manganese dioxide rapidly forms on a clean membrane and the enzyme deactivates only a little in each instance.

EXAMPLE 5

A 0.75 molar L-arginine solution is placed in an enzyme-membrane recycling reactor which has a a volume of 12 liters and 0.51 g manganese sulfate×H$_2$O (2.5×10$^{-4}$ molar), 0.53 g and 0.265 g ascorbic acid (2.5 and 1.25×10$^{-4}$ molar) as well as 60,000 units (5,000 units/l) calf's liver arginase are added and the pH is adjusted with sulfuric acid to 9.5. After 23 hours reaction time in the stationary recycle medium, the conversion was determined, the enzyme was separated with nitrogen pressure delivery via a 2.4 m$^2$ ultrafiltration hollow fiber module from the Romicon company and returned to the reaction in the next batch.

| | Initial pH 9.5 | | | |
|---|---|---|---|---|
| | Clean Membrane | | Clean Membrane | |
| Batch No. | Conversion (%) | Ascorbic Acid (mol/l) | Conversion (%) | Ascorbic Acid (mol/l) |
| 1 | 70 | 2.5 × 10$^{-4}$ | 88 | 1.25 × 10$^{-4}$ |
| 2 | 50 | 2.5 × 10$^{-4}$ | 86 | 1.25 × 10$^{-4}$ |
| 3 | 35 | 2.5 × 10$^{-4}$ | 90 | 1.25 × 10$^{-4}$ |
| 4 | 20 | 2.5 × 10$^{-4}$ | 84 | 1.25 × 10$^{-4}$ |
| 5 | 4 | 2.5 × 10$^{-4}$ | 84 | 1.25 × 10$^{-4}$ |
| 6 | 1.5 | 2.5 × 10$^{-4}$ | 84 | 1.25 × 10$^{-4}$ |
| 7 | 0 | 2.5 × 10$^{-4}$ | 83 | 1.25 × 10$^{-4}$ |
| 8 | — | | 84 | 1.25 × 10$^{-4}$ |

Given an equimolar addition of manganese sulfate, the enzyme deactivates rapidly whereas in the case of a semi-equivalent addition a slight loss of manganese dioxide was apparent after 23 hours and the arginase deactivated only slightly.

EXAMPLE 6

Production of L-ornithine acetate 42.3 mg manganese sulfate hydrate (2.5×10$^{-4}$ molar), 21.8 mg ascorbic acid (1.25×10$^{-4}$ molar) and 15000 units calf's liver arginase of the Boehringer Mannheim company were added to 1 liter of a 0.75 molar L-arginine solution. After 48 hours the conversion was 100% according to HPLC. The mixture was adjusted with acetic acid to pH 6.8, three quarters of the water drawn off and the ornithine acetate precipitated with one liter ethanol at room temperature. After 15 min. of postagitation the precipitate was filtered off, postwashed with ethanol and dried in a vacuum (40 mbars). The yield of pure ornithine acetate was 137.0 g, 95% of theory). Amount of rotation (c=5 in water)+10.0° (theoretical: +9.0 to +11.0).

EXAMPLE 7

| Arginase kit for 1 liter batch | |
|---|---|
| 10,000 units arginase | |
| 170 mg (1 mmole) | L-ornithine × HCl |
| 42.3 mg (0.25 mmole) | manganese sulfate × H$_2$O |
| 43.7 mg (0.125 mmole) | L-ascorbic acid |
| 174.2 g (1 mole) | L-arginine. |

The enzyme (in lyophilized form) and the L-ornithine are supplied in mixture in a vessel (ampoule) in which, in particular, the manganese sulfate and the ascorbic acid can also be mixed in. The arginine is normally put in separately but can also be present mixed in with the other components.

For the batch, everything is added to one liter of water and allowed to stand approximately 2 days.

What is claimed is:

1. In a method for the enzymatic production of L-ornithine from L-arginine in which L-arginine is converted to L-ornithine in an aqueous solution by means of mammalian liver L-arginase and L-arginase is recovered, the improvement in which ascorbic acid is present in dissolved form in the solution in at least 10-fold molar amount relative to the L-arginase, and conversion to L-ornithine takes place in quiescent solution.

2. The method according to claim 1 in which Mn$^{2+}$ is added to the aqueous solution.

3. The method according to claim 1 or claim 2 in which the aqueous solution contains a buffer system.

4. A method for the enzymatic production of L-ornithine from L-arginine comprising the steps of:

(i) converting L-arginine to L-ornithine in quiescent aqueous solution in the presence of a reducing agent and Mn$^{2+}$ by means of mammalian liver L-arginase, wherein the reducing agent lowers deactivation of the L-arginase and is dissolved in the solution in a molar amount which is at least 10-fold molar amount relative to the L-arginase, and wherein the molar ratio of Mn$^{2+}$ to reducing agent is a value greater than 1.0 and less than 100.0, such that there is a stoichiometric excess of Mn$^{2+}$, under such conditions that slow precipitation of manganese dioxide is assured; and (ii) recovering L-arginase.

5. The method according to claim 4 in which the reducing agent is present in a concentration of 10$^{-7}$ to 10$^{-1}$ moles/l.

6. The method according to claim 5 in which the pH is adjusted at the beginning of the L-arginase reaction to 10.5 to 11.5 and in which the reducing agent is added in a concentration of at least 10$^{-5}$ moles/l.

7. The method according to claim 4 in which, after the reaction, the reaction batch is separated by ultrafiltration into a filtrate containing dissolved components and into L-arginase with undissolved components of the reaction batch.

8. The method according to claim 7 in which MN$^{2+}$ is present during the enzymatic production of ornithene from arginine and is present with the arginine in undissolved form after ultrafiltration, wherein the molar ratio of MN$^{2+}$ to L-arginase is at least 10 to 1 said method including the step of separating the arginase after the ultrafiltration from the undissolved MnO$_2$.

9. The method according to claim 7 in which the filtrate is passed over an acidic ion exchanger, the latter is subsequently eluted, the eluate neutralized, adjusted, to a pH of approximately 8.9, concentrated by evaporation, and the L-ornithine is precipitated as a salt with ethanol.

* * * * *